(12) United States Patent
Mihan

(10) Patent No.: US 7,279,609 B2
(45) Date of Patent: Oct. 9, 2007

(54) METHOD FOR ALPHA-OLEFIN TRIMERIZATION

(75) Inventor: Shahram Mihan, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 663 days.

(21) Appl. No.: 10/488,932

(22) PCT Filed: Sep. 16, 2002

(86) PCT No.: PCT/EP02/10377

§ 371 (c)(1), (2), (4) Date: Mar. 15, 2004

(87) PCT Pub. No.: WO03/024902

PCT Pub. Date: Mar. 27, 2003

(65) Prior Publication Data

US 2004/0242946 A1    Dec. 2, 2004

(30) Foreign Application Priority Data

Sep. 15, 2001 (DE) ................ 101 45 619

(51) Int. Cl.
  *C07C 2/26* (2006.01)
  *C07C 2/04* (2006.01)
  *C07C 2/24* (2006.01)
(52) U.S. Cl. .................. 585/511; 585/510; 585/512
(58) Field of Classification Search ........ 585/510–512, 585/520–524
  See application file for complete search history.

(56) References Cited

U.S. PATENT DOCUMENTS

| 3,576,898 | A | | 4/1971 | Blake et al. | |
|---|---|---|---|---|---|
| 5,043,515 | A | * | 8/1991 | Slaugh et al. | 585/512 |
| 5,859,159 | A | * | 1/1999 | Rossi et al. | 526/170 |
| 2004/0097772 | A1 | | 5/2004 | Deckers et al. | |

FOREIGN PATENT DOCUMENTS

| EP | 0 268 214 | 5/1988 |
|---|---|---|
| EP | 0 366 212 | 5/1990 |
| EP | 0 562 258 | 9/1993 |
| FR | 2 488 259 | 2/1982 |
| WO | 01 96508 | 12/2001 |
| WO | WO 02/066405 | 8/2002 |

OTHER PUBLICATIONS

Claudio Pellecchia, et al. Makromol. Chem. Rapid Commun., vol. 13, pp. 277-281 1992.
Claudio Pellecchia, et al. Organometallics, vol. 12, pp. 4473-4478 1993.
Qinyan Wang, et al. Organometallics, vol. 15, pp. 693-703 1996.
Jörg Saßmannshausen, et al. Journal of Organometallic Chemistry, vol. 548, pp. 23-28 1997.
Qinyan Wang, et al. Macromolecules, vol. 28, pp. 8021-8027 1995.
Florin Barsan, et al. J. Chem. Soc., Chem. Commun., pp. 1065-1066 1995.
Jörg Saßmannshausen, et al. Journal of Organometallic Chemistry, vol. 592, pp. 84-94 1999.
Claudio Pellecchia, et al. Macromolecules, vol. 33, pp. 2807-2814 2000.
Randolf D. Köhn, et al. Angew. Chem. vol. 112, pp. 4519-4521 2000.
Claudio Pellecchia, et al. Macromolecules, vol. 32, pp. 4491-4493 1999.
Agnew. Chem. vol. 113, No. 13, pp. 2584-2587 2001.

* cited by examiner

*Primary Examiner*—Glenn Caldarola
*Assistant Examiner*—In Suk Bullock
(74) *Attorney, Agent, or Firm*—Oblon, Spivak, McClelland, Maier & Neustadt, P.C.

(57) ABSTRACT

The invention concerns a method for α-olefin trimerization comprising a number of carbon atoms not less than 3, by transforming an α-olefin or a hydrocarbon mixture containing α-olefins, at temperatures ranging between 0 and 150° C. and pressures ranging between 1 and 200 bars, in the presence of a catalyst. Said method uses a catalyst capable of being produced from: a) a compound of formula RMX3, wherein: R represents a cyclopentadienyl group whereof the hydrogen atoms can be partly or entirely substituted by identical or different alkyl groups and/or aryl groups, two substituents being capable of further forming a saturated or unsaturated hydrocarbon chain; M represents a titanium, zirconium or hafnium atom; and the groups X represent independently of one another extractable counter-ions; and b) at least an activating adjuvant. The invention further concerns the resulting trimers, alkanes capable of being produced with said trimers by hydrogenation, oxo-alcohols capable of being produced from said trimers, plasticizers and surfactants capable of being produced from said oxo-alcohols, as well as lubricants and fuel additives containing said trimers and/or said alkanes.

14 Claims, No Drawings

METHOD FOR ALPHA-OLEFIN TRIMERIZATION

BACKGROUND OF THE INVENTION

1. Field of the Invention

The present invention relates to a process for the trimerization of α-olefins of 3 or more carbon atoms by reacting an α-olefin or a hydrocarbon mixture which contains α-olefins at from 0 to 150° C. and from 1 to 200 bar in the presence of a catalyst.

2. Description of the Background

The present invention furthermore relates to the trimers thus obtainable, the alkanes obtainable by the trimers by hydrogenation, the oxo alcohols obtainable from the trimers, the plasticizers and surfactants obtainable from the oxo alcohols, and lubricants and fuel additives which contain the trimers and/or the alkanes.

Olefin trimers of up to 30 carbon atoms are of considerable economic importance as copolymers for plastics or as intermediates for oxo alcohols, the latter in turn being components of surfactants and plasticizers for plastics. Lubricants and fuel additives constitute a further field of use for such trimers. In the integrated product system of the chemical industry, trimerization processes are therefore a key step from industrial olefin streams which originate, for example, from the steam crackers to products of daily use.

Makromol. Chem., Rapid Communic. 13 (1992), 277 and organometallics 12 (1993), 4473 disclose that ethene and propene can be polymerized in the presence of the catalyst system comprising $B(C_6F_5)_3$ and $Cp'MR_3$ ($Cp'=C_5H_5$ or $C_5Me_5$, M=Ti or Zr, R=Me or $CH_2Ph$).

Furthermore, Organometallics 15 (1996), 693, J. Organomet. Chem. 548 (1997), 23, Macromolecules 28 (1995), 8021 and J. Chem. Soc., Chem. Commun. (1995), 1065 disclose the use of the catalyst system comprising $\eta^5\text{-}C_5Me_5TiMe_3$ and $B(C_6F_5)_3$ in the polymerization of olefins and styrene and of isobutene.

J. Organomet. Chem. 592 (1999), 84-94 describes the use of complexes of the type $(\eta^5\text{-}C_5H_4R)TiCl_3$ where R=$CMe_2Ph$, $CMe_2CH_2Ph$, $SiMe_2Ph$, $CHPh_2$), $(\eta^5\text{-}C_5H_4CMe_2CH_2Ph)ZrCl_3 \cdot dme$ and $(\eta^5\text{-}C_5H_4CHPh_2)Ti(CH_2Ph)_3$ in the polymerization of propene.

Macromolecules 33 (2000), 2807-2814 and Angew. Chem. 112 No. 23 (2000), 4519-4521 reports that the system $[C_5Me_5TiMe_3]/B(C_6F_5)_3$ catalyzes the cotrimerization of two ethene molecules with one styrene molecule, whereas the trimerization of an α-olefin as such is not possible therewith.

The catalyst system comprising $\eta^5\text{-}C_5Me_5TiMe_3$ and $B(C_6F_5)_3$ is also used, according to Macromolecules 32 (1999), 4491-4493, in the specific preparation of butyl-branched polyethylenes starting from ethene. 1-Hexene is observed as a byproduct there.

Angew. Chem. 113 No. 13 (2001), 2584-2587 discloses that $[(\eta^5\text{-}C_5H_4CMe_3)TiCl_3]$/methylaluminoxane is a polymerization catalyst whereas $[(\eta^5\text{-}C_5H_4CMe_2phenyl)TiCl_3]$/methylaluminoxane is a catalyst for the trimerization of ethene to 1-hexene.

However, the trimerization results achieved by means of the known processes on α-olefins of 3 or more carbon atoms are not yet satisfactory.

SUMMARY OF THE INVENTION

It is an object of the present invention to provide a process for the selective trimerization of α-olefins.

We have found that this object is achieved by a process for the trimerization of α-olefins of 3 or more carbon atoms by reacting an α-olefin or a hydrocarbon mixture which contains α-olefins at from 0 to 150° C. and from 1 to 200 bar in the presence of a catalyst, in which a catalyst which is obtainable from a) a compound $RMX_3$, in which
   R is a cyclopentadienyl group, some or all of whose hydrogen atoms can be substituted by identical or different alkyl groups and/or aryl groups, where 2 substituents together can also form a saturated or unsaturated hydrocarbon chain,
   M is titanium, zirconium or hafnium and
   the groups X, independently of one another, are abstractable opposite ions, and
b) at least one activating additive is used.

DETAILED DESCRIPTION OF THE PREFERRED EMBODIMENTS

Furthermore, the trimers thus obtainable, the alkanes obtainable via the trimers by hydrogenation, the oxo alcohols obtainable from the trimers, the plasticizers and surfactants obtainable from these oxo alcohols, and lubricants and fuel additives which contain the trimers and/or the alkanes have been found.

By means of the novel process, it is possible to obtain trimers of α-olefins of 3 or more carbon atoms in high yields and high selectivity.

Preferred α-olefins of 3, 4 or more carbon atoms are straight-chain and branched α-olefins of 4 to 22, preferably 3 to 12, carbon atoms. 1-Propene, 1-pentene, 1-hexene and 1-decene are particularly preferred and 1-butene is very particularly preferred.

Mixtures of the α-olefins with one another and/or with alkanes can also be used. In the novel process, α-olefin streams which substantially contain a single α-olefin and in addition one or more alkanes are preferably used. The use of a single α-olefin as such is particularly preferred.

Preferred groups R in the compounds RMX3 are cyclopentadienyl groups which may be substituted by identical or different by identical or different $C_1$- to $C_{22}$-alkyl groups, such as the methyl group, and those cyclopentadienyl groups in which 2, preferably neighboring carbon atoms of the cyclopentadienyl ring are linked to one another by a saturated or unsaturated carbon chain of, preferably, 4 carbon atoms, such as in indenyl and 1,2,3,4-tetra-hydroindenyl. Particularly preferred groups R are the pentamethylcyclopentadienyl group, the isopropylcyclopentadienyl group, the tetramethylcyclopentadienyl group and very particularly preferably the unsubstituted cyclopentadienyl group.

Preferred catalysts in the novel process are those in which M is titanium.

Preferred groups X in the compounds $RMX_3$ are:
halogen, such as fluorine, bromine, iodine and especially chlorine,
tosylate, triflate, tetrafluoroborate, tetrakis(pentafluorophenyl)borate, hexafluorophosphate, hexafluoroantimonate and tetraphenylborate,
$C_1$- to $C_{10}$-carboxyl, especially 2-ethylhexanoate,
alkyl, arylalkyl and aryl groups, such as methyl, ethyl, isopropyl, phenyl and benzyl,
bulky, noncoordinating anions, such as $B(C_6F_5)_4^-$.

The groups X are chosen in particular so that the compound $RMX_3$ containing them have good solubility in any solvent used.

Particularly preferred groups X are chlorine and tosylate, in particular chlorine.

In addition to the compounds $RMX_3$, their complexes with weakly bonded neutral complex ligands are also suitable, for example complexes of the type $[RML_3]X_3$, where L is, for example, tetrahydrofuran or triethylamine and X is, for example, tetrafluoroborate, hexafluoroantimonate or tetrakis(pentafluorophenyl)borate.

Here and below, alkyl and alkoxy having as a rule 1 to 20, preferably 1 to 8, especially 1 to 4, carbon atoms. Examples of alkyl are in particular methyl, ethyl, n-propyl, isopropyl, n-butyl, 2-butyl, isobutyl, tert-butyl, n-pentyl, n-hexyl, 2-hexyl, n-heptyl, 2-heptyl, n-octyl, 2-octyl and 2-ethylhex-1-yl. Examples of alkoxy are in particular methoxy, ethoxy, n-propoxy, isopropoxy, n-butoxy, 2-butoxy, isobutoxy, tert-butoxy, n-pentyloxy, n-hexyloxy, 2-hexyloxy, n-heptyloxy, 2-heptyloxy, n-octyloxy, 2-octyloxy and 2-ethylhex-1-yloxy.

In the novel process, the concentration of the compound $RMX_3$ is usually from $1\times10^{-7}$ to 1, preferably from $1\times10^{-6}$ to 0.1, in particular from $1\times10^{-5}$ to 0.01 mol per kg of the reaction mixture.

The concentration of activator compound is usually from $1\times10^{-8}$ to 500, preferably from $1\times10^{-7}$ to 10, in particular from $5\times10^{-5}$ to 2, especially up to 0.5 mol per kg of the reaction mixture, in the case of the alkylaluminoxane calculated as mol of Al/kg. Otherwise, a person skilled in the art optimizes the concentration of activator compound in particular with regard to the procedure in the process, reactor used and purity of the starting materials. It was observed that the amount of metal alkyl in the case of a relatively large batch is comparatively proportionately smaller than in the case of smaller batches.

Suitable activating additives are for example metal alkyls, some of whose alkyl groups can be replaced by halogen and/or alkoxy, and furthermore alkylaluminoxanes, boron compounds and mixtures of the abovementioned activators, for example combinations of metal alkyls, some of whose alkyl groups may be replaced by halogen and/or alkoxy, with boron compounds and combinations of alkylaluminoxanes with boron compounds.

The molar ratio of metal M to activator compound—in the case of alkylaluminoxane, the molar ratio of aluminum to metal M—is usually from 1:10 to 1:20 000, preferably from 1:50 to 1:1 000, in particular from 1:200 to 1:700 especially up to 1:500.

Among the metal alkyls which are used as activating additives, the alkylaluminums are preferred. Alkylaluminums, some of whose alkyl groups can be substituted by halogen and/or alkoxy are, for example, alkylaluminums of the formulae $AlR_3$, $AlR_2Hal$, $AlRHal_2$, $AlR_2OR'$, $AlRHalOR'$ and $Al_2R_3Hal_3$ and mixtures thereof, where R and R', independently of one another, are methyl, ethyl or a straight-chain or branched $C_3$- to $C_8$-alkyl group and Hal is fluorine, bromine, iodine or especially chlorine, for example trimethylaluminum, triethylaluminum, tri-n-propylaluminum, triisopropylaluminum, tributylaluminum, diethylaluminum chloride, diethylaluminum bromide, diethylaluminum ethoxide, diethylaluminum phenoxide or ethylaluminum methoxychloride. Alkylaluminums of the type $AlR_3$ and $AlRHal_2$ are preferably used, triethylaluminum alone or a mixture of triethylaluminum and ethylaluminum dichloride being particularly preferred.

As an alternative to metal alkyls, some of whose alkyl groups can be replaced by halogen and/or alkoxy, it is also possible to use mixtures of the corresponding metal alkyls and suitable cocatalysts, from which the metal alkyls, some of whose alkyl groups can be replaced by halogen and/or alkoxy, form in situ in the reactor.

Suitable cocatalysts here are alkyl halides, alkylsilicon halides and Lewis acid metal halides, such as tin tetrachloride, germanium chloride, aluminum trichloride and titanium tetrachloride. Preferred cocatalysts include n-butyl chloride, n-butyl iodide, trimethylsilyl chloride, trimethylsilyl bromide, tin tetrachloride, germanium chloride and especially n-butyl bromide.

In the system comprising metal alkyl, some of whose alkyl groups can be replaced by halogen and/or alkoxy, and cocatalyst, the two components are present in a molar ratio of from 1:3 to 30:1, preferably from 1:1 to 15:1.

In the novel process, the amount of the compound $RMX_3$ is usually from $1\times10^{-7}$ to 1, preferably from $1\times10^{-6}$ to 0.1, in particular from $1\times10^{-5}$ to 0.01, mol per kg of the reaction mixture.

The amount of the metal alkyl, some of whose alkyl groups can be replaced by halogen and/or alkoxy, is usually from $1\times10^{-8}$ to 500, preferably from $1\times10^{-7}$ to 10, in particular from $5\times10^{-5}$ to 0.5, mol per kg of the reaction mixture.

Preferred trimerization catalysts according to the invention are furthermore those which contain an alkylaluminoxane as the activating additive.

Suitable alkylaluminoxanes are disclosed, for example, in DE-A 30 07 725, their structures being substantially unclear. They are products of the careful partial hydrolysis of alkylaluminums (cf. DE-A 30 07 725). These products are evidently not present in pure form but as mixtures of open-chain and cyclic structures of the type IIa and IIb, which are presumably in dynamic equilibrium with one another.

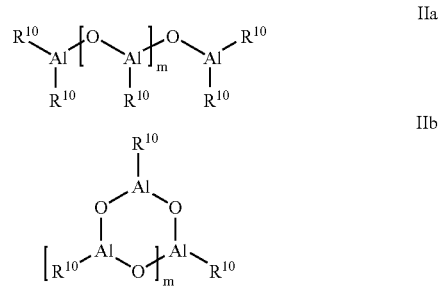

In the formulae IIa and IIb, the groups $R^{10}$ are identical or different and, independently of one another, are $C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl or sec-hexyl, particularly preferably methyl. m is an integer from 0 to 40, preferably from 0 to 25, particularly preferably from 0 to 22.

In the literature, cage-like structures for aluminoxanes are also discussed (cf. Organometallics 15 (1996), 2213-26; Macromol. Symp. 97 (1995), 15-25).

The alkylaluminoxanes display their activity as an activating additive in the context of the present invention independently of their structural characteristics.

The concentration of alkylaluminoxane is usually from $1\times10^{-8}$ to 500, preferably from $1\times10^{-7}$ to 10, in particular from $5\times10^{-5}$ to 2, especially up to 0.5 mol per kg of the reaction mixture. The ratio of compound $RMX_3$ to the activating alkylaluminoxane is as a rule from 1:10 to 1:20 000, preferably from 1:50 to 1:1 000, in particular from 1:200 to 1:700, especially up to 1:500, calculated as the molar ratio of metal M to aluminum.

Examples of boron compounds suitable as activators are triarylboranes and salts of tetrakisaryl borates, preferably those having electron-attracting aryl radicals. Here, aryl is preferably carbocyclic aryl, in particular phenyl, which preferably has 1, 2, 3, 4 or 5 electron-attracting substituents, such as fluorine and perfluoroalkyl, such as trifluoromethyl (or perfluoromethyl). Particularly preferred opposite ions for the borate are tertiary and quaternary ammonium ions, such as dibutylammonium and N,N-dimethylanilinium, and the tritylium ion ($=[(C_6H_5)_3C]^+$). Examples of preferred electron-attracting aryl radicals are pentafluorophenyl and 3,5-bis(perfluoromethyl)-phenyl. Examples of particularly preferred boron compounds having electron-attracting radicals are trispentafluorophenylborane, N,N-dimethylanilinium tetrakispentafluorophenylborate, tri-n-butylammonium tetrakispentafluorophenylborate, N,N-dimethylanilinium tetrakis-(3,5-bisperfluoromethyl)phenylborate, tri-n-butylammonium tetrakis(3,5-bisperfluoromethyl)phenylborate and tritylium tetrakispentafluorophenylborate). These boron compounds are disclosed in EP-A 468 537 and EP-A 426 638. Tritylium tetrakispentafluorophenylborate, trispentafluorophenylborane and especially dimethylanilinium tetrakis(pentafluorophenyl)borate are preferred.

In a further preferred embodiment of the novel process, a trimerization catalyst which contains, as the activating additive, at least one boron compound and at least one alkylaluminum, some of whose alkyl groups may be replaced by halogen and/or alkoxy, and/or at least one alkylaluminoxane is used.

In these embodiments, in particular the abovementioned boron compounds having electron-attracting radicals (e.g. trispentafluorophenylborane, N,N-dimethylanilinium tetrakispentafluorophenylborate, tri-n-butylammonium tetrakispentafluorophenylborate, N,N-dimethylanilinium tetrakis (3,5-bisperfluoromethyl)phenylborate, tri-n-butylammonium tetrakis(3,5-bisperfluoromethyl) phenylborate and tritylium tetrakispentafluorophenylborate) are suitable for this purpose. These boron compounds are disclosed in EP-A 468 537 and EP-A 426 638. Tritylium tetrakispentafluorophenylborate, trispentafluorophenylborane and especially dimethylanilinium tetrakis(pentafluorophenyl)borate are preferred.

The amount of the activating boron compound used is dependent on its nature. The molar ratio of compound $RMX_3$ to the activating boron compound is as a rule from 1:1 to 1:50, preferably from 1:1 to 1:10. Regarding the concentration of $RMX_3$ and metal alkyl or alkylaluminoxane and regarding the molar ratio of $RMX_3$ to metal alkyl or alkylaluminoxane, the statements made above are applicable.

Suitable alkylaluminums, some of whose alkyl groups may be replaced by halogen and/or alkoxy, and alkylaluminoxanes are those members of these classes of substances which are mentioned further above, in the amounts stated there, based on the compound $RMX_3$.

The preparation of the catalysts is otherwise generally known (cf. Organometallics 8 (1989), 476, and literature cited in Macromolecules 33 (2000), 2813, under Experimental Section) and therefore requires no further explanations. Some of the catalysts are also commercially available (for example from Aldrich).

The novel process is carried out as a rule in a solvent. Aprotic solvents are preferred. In particular, the solvents contain no water or only extremely little water and/or traces of alcohol. Examples of suitable solvents include straight-chain, branched or alicyclic saturated hydrocarbons of 1 to 20 carbon atoms, such as butane, pentane, 3-methylpentane, hexane, heptane, 2-methylhexane, octane, cyclohexane, methylcyclohexane, 2,2,4-trimethylpentane or decalin, straight-chain or branched halogenated hydrocarbons, such as dichloroethane, aromatic hydrocarbons, such as benzene, toluene, xylene, ethylbenzene, mesitylene or tetralin, and the oligomeric reaction products which are liquid under the reaction conditions are used. Mixtures of the abovementioned solvents are also suitable. Preferred solvents are aromatic hydrocarbons and mixtures of aprotic solvents which predominantly comprise aromatic hydrocarbons, i.e. in an amount of more than 50, in particular more than 90, % by volume and in particular toluene in an amount of more than 50, in particular more than 90, % by volume.

Suitable solvents, in particular with the use of a trimerization catalyst, comprising $RMX_3$ and alkylaluminoxane, are aprotic solvents, for example the aliphatic and in particular the aromatic hydrocarbons mentioned above as solvents, and especially toluene and mixtures of aprotic solvent which comprise more than 50, in particular more than 90, % by volume of aromatic hydrocarbons and in particular more than 50, in particular more than 90, % by volume of toluene.

Suitable solvents when using a trimerization catalyst which comprises, as the activating additive, at least one boron compound and at least one alkylaluminum, some of whose alkyl groups may be replaced by halogen and/or alkoxy, are aprotic solvents, for example the aliphatic or aromatic hydrocarbons mentioned further above as solvents, and especially toluene and the mixtures which contain more than 50, in particular more than 90, % by volume of aromatic hydrocarbons and in particular more than 50, especially more than 90, % by volume of toluene.

In particular because of the tendency of in particular the metal alkyls and especially the aluminum compounds and possibly the cocatalysts to hydrolyze, the trimerization should, as a rule, be carried out with very substantial exclusion of moisture. Working methods known per se are used. The procedure is preferably carried out under inert gas and using apparatuses which have been thoroughly heated. The inert gases used may be all gases which are chemically inert under the reaction conditions, expediently nitrogen or argon. In addition, the α-olefin to be reacted may itself form the function of the inert gas, provided that it has a sufficiently high vapor pressure under the reaction conditions.

The trimerization is preferably carried out at from 1 to 120° C., in particular from 20 to 110° C. The pressure is preferably from 1 to 120 bar. The pressure is expediently chosen so that the starting mixture is present in liquid form at the set temperature. Furthermore, a person skilled in the art can readily establish an optimum productivity by a few routinely performed experiments at temperatures and pressures in the stated ranges and by setting a heat removal appropriate in each case.

In the case of α-olefins which are present in gaseous form at the reaction temperature, the reaction can be operated either at atmospheric pressure or under superatmospheric pressure. When carried out at atmospheric pressure the α-olefin is usually passed through a solution of the catalyst in a suitable solvent, preferably with thorough mixing. In the variant under pressure, a pressure at which it is present in the condensed, i.e. liquid, phase is preferably used. It has frequently proven advantageous additionally to use an inert gas, such as nitrogen, for establishing the pressure.

The novel process can be carried out batchwise or continuously, the continuous procedure being preferred on an industrial scale.

The reactors suitable for carrying out the reaction continuously by the novel process are familiar to a person skilled in the art, for example from Ullmann's Enzyklopädie der technischen Chemie, Volume 1, 3rd Edition, 1951, page 743 et seq.; pressure-resistant reactors are described there on page 769 et seq.

The other boundary conditions of the trimerization process are established by a person skilled in the art on the basis of his general technical knowledge (in this context, cf. for example DE-A 196 07 888).

For the catalyst deactivation at the end of the reaction, for example, water and monoalcohols of 1 to 10 carbon atoms are suitable, it being possible to add to these substances mineral acids and polar substances which are conventional inhibitors for transition metal catalysts, such as carbon monoxide, carbon dioxide, carbon disulfide, hydrogen sulfide and ammonia.

The products of the novel process are expediently purified by distillation.

In order to achieve a high overall conversion, unconverted α-olefin can be recovered and recycled to the reaction.

The trimers obtainable by the novel process are particularly suitable for the preparation of monoalcohols for plasticizers and surfactants. For this purpose, the trimers are expediently subjected to the hydroformylation which gives mixtures of the aldehydes and alcohols whose chain has been extended by one carbon atom and which are then hydrogenated to give the desired alcohols. The manner in which the hydroformylation and hydrogenation are carried out is known per se to a person skilled in the art and therefore requires no further explanations (cf. for example Beller et al., Journal of Molecular Catalysis A 104 (1995), 17-85).

Furthermore, the trimers can be hydrogenated by processes known per se to give the corresponding alkanes.

The examples which follow illustrate the invention.

EXAMPLES 1 TO 9

Cyclopentadienyltitanium trichloride ($CpTiCl_3$) was dissolved at 40° C. in toluene dried over sodium metal. Methylaluminoxane (MAO, from Witco) in the form of a 4.75 molar solution in toluene was added to the solution thus obtained (regarding the concomitant use of borate, cf. footnote 2 to table 1, see below). An excess of the respective α-olefin was metered into the resulting solution over a period of 60 minutes at the temperature T. Thereafter, a mixture of 15 ml of concentrated hydrochloric acid and 15 ml of methanol was added and stirring was carried out for 15 minutes. A further 250 ml of methanol were then added and the mixture was stirred. The solution was then filtered to remove the precipitated polymer. The filtrate was washed with water and dried over sodium sulfate. The composition of the filtrate was determined by means of quantitative gas chromatography.

Table 1 below shows the substances used, the associated amounts and the essential reaction parameters and experimental results.

TABLE 1

Data for examples 1-10

| Ex. | Monomer | Amount of toluene [ml] | Amount of $CpTiCl_3$ [mg] | ($\mu$mol) | Atomic ratio Ti:Al:B | T [° C.] |
|---|---|---|---|---|---|---|
| 1 (Comparison) | Ethene | 250 | 54.3 | 247.6 | 1:500:— | 40 |
| 2 | 1-Butene | 250 | 44.1 | 201.1 | 1:100:— | 40 |
| 3 | 1-Butene | 500[1] | 47.6 | 217.1 | 1:300:— | 40 |
| 4 | 1-Butene | 250[1] | 48.2 | 219.8 | 1:500:— | 20 |
| 5 | 1-Butene | 250 | 52.1 | 237.6 | 1:500:— | 40 |
| 6 | 1-Butene | 250 | 55.0 | 250.8 | 1:1000:— | 40 |
| 7 | 1-Butene | 250[2] | 32.6 | 148.6 | 1:50:1.3 | 40 |
| 8 | 1-Hexene | 250 | 49.3 | 224.8 | 1:500:— | 40 |
| 9 | 1-Decene | 250 | 56.1 | 255.8 | 1:500:— | 40 |

| Ex. | $<C_{10}$ | $C_{10}$ | $C_{12}$ | $C_{14}$ | $C_{16}$ | $C_{18}$ | $C_{20}$ | $C_{30}$ | Polymer |
|---|---|---|---|---|---|---|---|---|---|
| | | | | Products [g] | | | | | |
| 1 | $C_6$: 1.04 | 0.4 | — | — | — | — | — | | 1.1 |
| 2 | — | — | 0.89 | — | 0.06 | — | — | | — |
| 3 | — | — | 2.71 | — | 0.07 | — | — | | — |
| 4 | — | — | 3.62 | 0.19 | 0.04 | 0.04 | — | | — |
| 5 | — | — | 4.25 | 0.11 | — | — | — | | — |
| 6 | — | — | 7.61 | — | 0.29 | — | 0.05 | | — |
| 7 | — | — | 0.2 | — | 0.03 | — | — | | — |
| 8 | — | — | 1.46 | — | — | 0.86 | — | | — |
| 9 | — | — | — | — | — | — | — | 0.94 | — |

| Ex. | $<C_{10}$ | $C_{10}$ | $C_{12}$ | $C_{14}$ | $C_{16}$ | $C_{18}$ | $C_{20}$ | Polymer | Total |
|---|---|---|---|---|---|---|---|---|---|
| | | | Activity of the catalyst used [kg/(mol Ti * h)] | | | | | | |
| 1 | $C_6$: 4.2 | 1.6 | — | — | — | — | — | 4.4 | 10.2 |
| 2 | — | — | 4.43 | — | 0.3 | — | — | — | 4.73 |
| 3 | — | — | 12.5 | — | 0.32 | — | — | — | 12.82 |
| 4 | — | — | 16.5 | 0.86 | 0.18 | 0.18 | — | — | 17.72 |
| 5 | — | — | 17.9 | 0.46 | — | — | — | — | 18.36 |
| 6 | — | — | 30.3 | — | 1.16 | — | 0.2 | — | 31.66 |
| 7 | — | — | 1.35 | — | 0.2 | — | — | — | 1.55 |
| 8 | — | — | 6.49 | — | — | 3.83 | — | — | 10.32 |
| 9 | — | — | — | — | — | — | 3.7 | — | 3.7 |

[1] $CpTiCl_3$ was dissolved in 50 ml of toluene and then MAO was added, followed by the remaining amount of toluene
[2] $CpTiCl_3$, dimethylanilinium tetrakispentafluorophenylborate and toluene were combined at 75° C. and triethylaluminum was then added at 40° C.

EXAMPLE 10

An autoclave flushed with argon was heated under reduced pressure for 60 minutes at 140° C. A solution of 11.4 mg of $CpTiCl_3$ in 5 ml of anhydrous toluene (obtainable from Aldrich) was initially taken therein under an argon atmosphere and then 6.4 g of a 30% by weight solution of methylaluminoxane in toluene were added. Thereafter, 10 g of 1-butene were introduced into the autoclave via a lock and a pressure of 10 bar was established with nitrogen and heating to 40° C. was effected. After one hour, cooling was carried out, the autoclave was let down to atmospheric presure and 1.14 g of octane were added to the reaction mixture. While cooling with an ice bath, 5 ml of a 5% strength by weight aqueous hydrochloric acid were added for deactivation. The organic phase was investigated in the usual manner by gas chromatography. Dodenes (isomers) were formed with a selectivity of 86% and with a productivity of 0.75 kg of C12-isomers per g of titanium.

EXAMPLE 11

An oligomerization of 1-butene was carried out analogously to example 10, 14.4 mg of pentamethylcyclopentadienyltitanium trichloride being used instead of CpTiCl$_3$. Dodenes (isomers) were formed with a selectivity of 81% and with a productivity of 0.26 kg of C12-isomers per g of titanium.

EXAMPLE 12

An oligomerization of 1-butene was carried out analogously to example 10, 6.6 mg of isopropylcyclopentadienyltitanium trichloride being used instead of CpTiCl$_3$. In contrast to example 10, 1.93 g of 30% strength by weight methylaluminoxane solution and 20 ml of 1-butene were used and the reaction was carried out at 60° C. Dodenes (isomers) were formed with a selectivity of 78% and with a productivity of 0.76 kg of C12-isomers per g of titanium.

We claim:

1. A process for the trimerization of α-olefins of 3 or more carbon atoms, comprising:
   reacting an α-olefin of 3 or more carbon atoms or a hydrocarbon mixture which contains α-olefins at a temperature ranging from 0 to 150° C. and a pressure ranging from 1 to 200 bar in the presence of a catalyst, which is a combination of:
   a) a compound RMX$_3$, wherein R is a cyclopentadienyl group, some or all of whose hydrogen atoms are optionally substituted by identical or different alkyl groups, and/or aryl groups, and wherein 2 substituents together optionally form a saturated or unsaturated hydrocarbon chain, M is titanium, zirconium or hafnium, and the groups X, independently of one another, are abstractable opposite ions, and
   b) at least one activating additive, which is selected from the group consisting of metal alkyls, some of whose alkyl groups are optionally replaced by halogen and/or alkoxy, alkylaluminoxanes, boron compounds and mixtures thereof, thereby effecting the trimerization of the α-olefin reactant.

2. The process as claimed in claim 1, wherein the activating additive comprises at least one metal alkyl, some of whose alkyl groups are optionally replaced by halogen and/or alkoxy.

3. The process as claimed in claim 2, wherein the activating additive is an alkylaluminum, some of whose alkyl groups are optionally replaced by halogen and/or alkoxy.

4. The process as claimed in claim 1, wherein the activating additive comprises at least one boron compound in combination with at least one metal alkyl, some of whose alkyl groups are optionally replaced by halogen and/or alkoxy.

5. The process as claimed in claim 1, wherein the activating additive comprises at least one alkylaluminoxane.

6. The process as claimed in claim 1, wherein the activating additive comprises at least one boron compound and at least one alkylaluminoxane.

7. The process as claimed in claim 1, wherein said α-olefin is virtually free of other olefins.

8. The process as claimed in claim 1, wherein said α-olefin is a straight-chain or branched α-olefin containing from 4 to 22 carbon atoms.

9. The process as claimed in claim 8, wherein said α-olefin is 1-propene, 1-butene, 1-pentene, 1-hexene or 1-decene.

10. The process as claimed in claim 8, wherein group X is a halogen, tosylate, triflate, tetrafluoroborate, tetrakis(pentafluorophenyl)borate, hexafluorophosphate, hexafluoroantimonate, tetraphenylborate, $C_1$-$C_{10}$-carboxyl, alkyl, arylalkyl, aryl and a noncoordinating anion.

11. The process as claimed in claim 10, wherein X is chlorine.

12. The process as claimed in claim 1, wherein compound RMX$_3$ of the catalyst is present in the trimerization medium in an amount ranging from $1 \times 10^{-7}$ to 1 mol per kg of the trimerization medium.

13. The process as claimed in claim 1, wherein the activator compound is present in the trimerization medium in an amount ranging from $1 \times 10^{-8}$ to 500 mol per kg of the trimerization medium.

14. The process as claimed in claim 1, wherein the molar ratio of metal M of RMX$_3$, in the event the activator compound is an alkylaluminoxane, ranges from 1:10 to 1:20,000 in the trimerization medium.

* * * * *